United States Patent [19]

Glivicky et al.

[11] Patent Number: 4,675,463

[45] Date of Patent: Jun. 23, 1987

[54] PROCESS FOR REDUCING FOULING IN HIGHER OLEFIN PLANTS

[75] Inventors: Alexandr P. Glivicky; Donald J. Norris, both of Sarnia, Canada

[73] Assignee: Exxon Chemical Patents Inc., Linden, N.J.

[21] Appl. No.: 826,243

[22] Filed: Feb. 5, 1986

[51] Int. Cl.$^4$ ............................ C07C 2/14; C07C 7/12
[52] U.S. Cl. .................................... 585/514; 585/529; 585/820; 585/823; 585/824
[58] Field of Search ............... 585/514, 529, 517, 824, 585/823, 820

[56] References Cited

U.S. PATENT DOCUMENTS

| | | | |
|---|---|---|---|
| 2,478,897 | 8/1949 | Corson | 585/824 |
| 2,478,900 | 8/1949 | D'Ouville | 585/824 |
| 2,586,852 | 11/1947 | Morrell | 585/514 |
| 2,713,560 | 3/1951 | Morrell | 585/514 |

FOREIGN PATENT DOCUMENTS

| | | | |
|---|---|---|---|
| 154567 | 3/1951 | Australia | 585/529 |
| 507337 | 11/1954 | Canada | 585/514 |
| 544240 | 7/1957 | Canada | 585/517 |

OTHER PUBLICATIONS

*Hydrocarbon Processing*, vol. 47, p. 170, (Sep. '68).
*Petroleum Refiner*, vol. 39, p. 232, (1960).

Primary Examiner—Andrew H. Metz
Assistant Examiner—A. Pal
Attorney, Agent, or Firm—J. B. Murray, Jr.; J. J. Mahon

[57] ABSTRACT

An improved process for oligomerizing olefins is provided in which olefin feed is contacted with phosphoric acid catalyst to form an olefin oligomerization product containing phosphorous-containing foulant precursors. The olefin oligomerization product is then contacted with a foulant adsorbent comprising at least one member selected from the group consisting of alumina, activated alumina and magnesium oxide in an amount and under conditions sufficient to effect removal of at least a portion of said foulant precursors. The treated olefin oligomerization product stream can then be passed to downstream recovery and process equipment with minimized fouling.

7 Claims, No Drawings

PROCESS FOR REDUCING FOULING IN HIGHER OLEFIN PLANTS

BACKGROUND OF THE INVENTION

Field of the Invention

Higher olefins (e.g., acyclic alkenes of from 5 to 15+ carbon atoms) are produced commercially in large volumes by oligomerization over phosphoric acid catalysts using lower olefin feeds (for example, propylene, butenes and pentenes). *Hydrocarbon Processing*, vol. 47, page 170 (September 1968); *Petroleum Refiner*, vol. 36, no. 9, page 232 (1960). Prior art phosphoric acid catalysts which have been developed have employed a wide variety of catalyst supports, e.g. those disclosed in U.S. Pat. Nos. 2,586,852 and 2,713,560 (each to Morrell), phosphoric acid on such supports as activated carbon, silica gel, diatomaceous earth, kieselguhr, infusorial earth, bentonite, montmorillonite and similar adsorbent substances. This patentee also discloses that catalysts can be formed by baking at elevated temperature a mixture of kaolin and phosphoric acids (e.g., orthophosphoric, pyrophosphoric, metaphosphoric, and tetraphosphoric acids), and that the porosity of such kaolin catalysts can be improved by adding from 1 to 10% (based on the kaolin) by weight of calcium and/or magnesium oxides, or the corresponding carbonates, to the kaolin before mixing in the phosphoric acid. It is noted in these patents that mixtures of calcium oxide and magnesium oxide are preferred, because the former produces a more porous product but one which is softer and takes up water quite readily, whereas these features are corrected by the magnesium.

Equipment fouling in such higher olefins plants has been a serious problem since the 1930's. Heretofore, equipment sparing was thought to be the only means to effectively combat this problem. This has necessitated maintaining multiple trains of vital equipment to enable continued plant operation while simultaneously cleaning fouled equipment that have been taken out of service. The debits associated with fouling for each higher olefins plant range from thousands to millions of dollars per year depending on several factors, among these, availability of spare heat exchangers, distillation towers, maintenance costs, frequency of re-tubing of reactors and exchangers, etc.

Past attempts to minimize the degree of fouling (e.g., using neutralization, filtration and percolation) have met little success. Also, attempts have been made to introduce organic anti-foulants into process streams, but these have not created satisfactory solutions to the fouling in downstream equipment.

Canadian Pat. No. 507,337 is directed to a method of inhibiting metal corrosion in a polymerization reactor employing a bulk liquid phosphoric acid catalyst wherein phosphoric acid esters (reaction products of phosphoric acid and the feed olefins and/or the olefinic oligomerization products) are maintained in the reaction mixture below about 0.08 mol of such esters per mol of free phosphoric acid. In the process, the olefin feed is dried (e.g., with silica or alumina), heated and then introduced into the reactor. The reactor's liquid effluent is withdrawn and phase separated to form a lower phosphoric acid phase (which is recycled to the reactor) and an upper hydrocarbon phase, which is treated for product recovery. A portion of the separated phosphoric acid phase is heated in a separate vessel to thermally decompose the phosphoric acid esters. However, this method can result in fouling of the heat treatment vessel and only addresses corrosion problems in the reactor. No provision is made for avoiding of fouling in downstream hydrocarbon processing equipment. Moreover, thermal treatment of the separated hydrocarbon phase could result in undesired loss of hydrocarbon product, due to increased polymerizations catalyzed by the phosphoric acid thermal decomposition by-products.

SUMMARY OF THE INVENTION

It has now been found that fouling in higher olefins plants can be greatly minimized by contacting the olefin oligomerization effluent from the oligomerization reaction zone with a solid alumina, activated alumina or magnesium oxide in an amount and under conditions sufficient to remove phosphoric acid esters therefrom. It has been surprisingly found that alumina, activated alumina and magnesium oxide efficiently reduce the foulant precursors, thereby greatly extending the useful service life of equipment downstream of the olefin oligomerization reaction zone.

Without being bound thereby, it is believed that the lower olefins present in the olefin feed to the oligomerization reactor react with phosphoric acid present in the catalyst together with water in the olefin feed to produce phosphoric acid esters, and that these phosphoric acid esters pass into the reactor effluent and initiate further olefin polymerization on the walls of downstream process equipment. This additional polymerization of the olefins is believed to lead to high molecular weight fouling materials, which deposits on the walls of process equipment, impeding the ability of heat transfer equipment and impairing fluid flow therethrough.

DETAILED DESCRIPTION OF THE INVENTION

In the conventional higher olefins process, the selected lower olefin is reacted over a solid phosphoric acid catalyst to produce branched mono-olefins of a higher carbon number. These mono-olefins so produced are used as feedstock for hydroformylation to form oxo-aldehydes (which can be subsequently hydrogenated to the corresponding oxo-alcohols and used as intermediates to form phthalate plasticizers, and which can also be employed as detergent intermediates, such as nonyl phenol and dodecyl benzene). The lower olefins which can be used can comprise propylene, butenes and pentenes, or mixtures of the foregoing. For example, propylene and butenes from steam cracking and catalytic petroleum cracking are suitable mixtures. Any of the isomeric olefins can be used, alone or as mixtures. The olefin feedstock is typically first treated to remove deleterious quantities of impurities such as organic sulfur, sulfur compounds, acetylenic compounds and diolefins (e.g., hydrogen sulfide, mercaptans, methyl acetylene, propadiene and the like). Such a feedstock pretreatment can conventionally involve absorption of the impurities with mono- or diethanolamine and caustic wash stages for sulfur removal followed by selective catalytic hydrogenation to reduce the diolefins and acetylenes content.

In addition to the olefin, paraffins and water are also generally introduced. The paraffins can suitably comprise propane, butane, and pentane, with the selected paraffin generally comprising a molecule of the same molecular structure as the selected olefin (e.g., propane for propylene feeds, butane for butylene feeds, and the like). The function of the propane is as a diluent of the olefin feed to prevent excessive catalyst temperatures from being achieved within the reactor, and thereby control undesired exotherms. In addition, water is typically employed in the olefin feed, and the water content is maintained at a level which is selected to control the hydration level of the phosphoric acid catalyst. Such a hydration level control is important to maintain activity and life of the phosphoric acid catalyst. Typically, olefin feeds to such an oligomerization reactor will comprise from about 20 to 60 wt. % olefin, from about 40 to 80 wt. % paraffin, and from about 0.01 to 0.07 wt. % water, and more typically from about 30 to 40 wt. % olefin, from about 60 to 70 wt. % paraffin, and from about 0.02 to 0.04 wt. % water. However, the quantity of paraffin and water, and amounts of olefin, can vary widely depending on the olefin selected, the temperature and pressures to be employed in the oligomerization reactor, the precise products which are sought to be formed, the type of reactor which is employed and other factors.

Generally, the oligomerization reaction is conducted at a temperature of from about 150° to 230° C., more typically from about 165° to 215° C., and at a pressure of from about 4100 to 8200 kPa, more typically from about 4800 to 7000 kPa. Again, the precise temperature and pressure employed in the olefin oligomerization reactor will depend on a large number of factors, among them the type of olefin which is fed, the olefin distribution of products which is sought to be formed, and other factors.

The olefins can be passed to the reactor in either the liquid or vapor form, and feed rates are generally in the range of from about 1 to 3.5 liters/kg-hr, more typically from about 2 to 3 liters/kg-hr.

Since the oligomerization reaction is exothermic, the desired reaction temperature is conventionally maintained either by quenching with the selected paraffin gas, as by quenching between the catalyst stages when the reactor comprises a multistage vessel containing catalysts, or by conducting the reaction in a tubular reactor in which the phosphoric acid is contained within a plurality of parallel arranged tubes and around which cooling water is circulated for steam generation in order to remove the desired quantity of heat.

The solid phosphoric acid catalyst is conventional and can comprise phosphoric acid on silica gel or of other materials of a silicous character, including diatomacous earth, kieselguhr and the like. Such conventional phosphoric acid catalysts are disclosed in U.S. Pat. Nos. 2,586,852 and 2,713,560, the disclosures of which are hereby incorporated by reference.

According to the improvement of the process of this invention, the oligomerization product stream, after withdrawal of the product stream from the catalyst bed/tubes, is contacted with alumina, activated alumina and/or magnesium oxide in an amount and under conditions sufficient to remove at least a portion (and preferably at least about 20 wt. %, and more preferably at least about 50 wt. %, and most preferably from about 50 to 80 wt. %) of phosphorous-containing moieties in said product stream, preferably to achieve a concentration of phosphorous impurities in the treated product stream of less than about 100 ppm by weight, more preferably less than about 50 ppm by weight and most preferably less than about 20 ppm by weight. Generally, the amount of the alumina, activated alumina and/or magnesium oxides will typically comprise from about 0.01 to 1.0 part by weight, more preferably from about 0.05 to 0.2 part by weight, per part by weight of the oligomerization catalyst.

By "activated alumina" we mean alumina which has been activated by conventional methods of thermally treating granules of hydrated alumina. Illustrative of suitable activated aluminas are: activated alumina F1 (Aluminum Company of America, Pittsburgh, Pennsylvania), and activated alumina A-201 (Kaiser Aluminum and Chemical Corporation, Baton Rouge, La.). The particle size of the aluminas, activated aluminas and magnesium oxides can vary widely and will generally range from about 325 mesh to 5 cm in size, and the surface area of the activated alumina will generally range from about 200 to 400 square meters per gram. Suitable magnesium oxide solids are those containing at least 97 wt. % magnesium oxide, with the balance comprising calcium oxide, silica and iron oxide.

The oligomerization product stream can be treated according to the foulant removal step of this invention in a separate vessel after removal of the product stream from the oligomerization reactor or within the reactor, but after the removal of the product stream from contact with the polymerization catalysts, e.g., by placing the selected alumina, activated alumina, and/or magnesium oxide foulant adsorbent of this invention as a separate, lower layer of solids within a conventional downflow chamber reactor, on top of which solids is placed the polymerization catalyst. When the foulant adsorbent is employed in the lower section of the reactor, the olefin feed will be introduced to the upper portion of the reactor for oligomerization over the phosphoric acid catalyst, and the resulting product stream then will contact the foulant adsorbent after removal from the oligomerization reaction zone in the reactor. Such a lower layer of foulant adsorbent should possess suitable particle size, and crush strength (e.g., $\geq 10$ kg) properties to avoid undesired pressure drops over this lower layer. The defoulant adsorbent can also be positioned above the phosphoric acid for reactors which are operated in an upflow mode, with the olefin feed being introduced at the reactor's lower portion for withdrawal of the product stream from the reactor's upper sections.

The process of the present invention can be further illustrated by reference to the following examples, wherein parts are by weight unless otherwise indicated.

EXAMPLES

In a series of batch experiments, 100 cc of an olefin oligomerization reactor effluent, produced by a conventional olefin oligomerization of a propylene feed over phosphoric acid on kieselguhr catalyst (at 205° C. and 5 MPa) and comprising about 90 wt. % of $C_5$ to $C_{12}$ olefins and 10 wt. % $C_5$ to $C_8$ paraffins, and containing 134 wppm phosphorous impurities, was placed in a glass vessel containing the selected quantity of the indicated solid materials. The contents of the glass vessel were stirred for two hours. The liquid was then separated after allowing the solids to settle, and the liquids were analyzed for residual phosphorous impurities.

The data thereby obtained are set forth in Table I below:

TABLE I

| Run No. | Solid Material | Grams | Residual Fouling Precursor (ppm)* | | | | % Reduction |
|---|---|---|---|---|---|---|---|
| | | | (PA) | (TMP) | (DEP) | Total | |
| 1 | Activated Carbon (1) | 5.0 | 82 | 41 | — | 123 | 9 |
| 2 | Activated Carbon (2) | 5.0 | 80 | 36 | 38 | 154 | 0 |
| 3 | Silica (3) | 5.0 | 65 | 68 | — | 133 | 0 |
| 4 | Alumina (4) | 0.5 | 16 | — | — | 16 | 88 |
| 5 | Alumina (4) | 1.0 | 10 | <1 | 6 | <17 | 87 |
| 6 | Alumina (4) | 5.0 | 4 | <1 | — | <5 | 96 |
| 7 | Activated Alumina (5) | 0.5 | — | — | — | — | 100 |
| 8 | Activated Alumina (5) | 1.0 | — | <1 | — | <1 | 99 |
| 9 | Activated Alumina (5) | 5.0 | — | — | — | — | 100 |
| 10 | Magnesium oxide (6) | 0.5 | <1 | — | — | — | 99 |
| 11 | Magnesium oxide (6) | 1.0 | <1 | 14 | — | <15 | 89 |
| 12 | Magnesium oxide (6) | 5.0 | — | 6 | — | 6 | 96 |

Notes:
PA = $H_3PO_4$; TMP = $(CH_3O)_3P$; DEP = $(C_2H_5O)_2PO_2H$
(1) Filtrasorb 200 (950 $m^2$/gm); Calgon.
(2) Filtrasorb 400 (1150 $m^2$/gm); Calgon.
(3) Chromatographic grade silica (500 $m^2$/gm).
(4) Chromatographic grade Fisher Scientific Company (200 $m^2$/gm).
(5) Alcoa F-1 alumina (92% $Al_2O_3$; 210 $m^2$/g).
(6) 0.2 $m^2$/gm; Technical grade MagChem 10 ™ (Martin Marietta Chemicals).
*Foulant levels remaining determined after contacting the absorbents with 100 $cm^3$ of the liquid feed.

Therefore, it was surprisingly found that activated carbon and silica (despite these materials' high surface areas) are ineffective for removal of such fouling precursors; whereas alumina, activated alumina and magnesium oxide efficiently removed substantially all of these residual fouling precursors, with activated alumina being particularly effective.

From the foregoing description, one skilled in the art can easily ascertain the essential characteristics of this invention and without departing from the spirit and scope thereof can make various changes and/or modifications to the invention for adapting it to various usages and conditions. Accordingly, such changes and modifications are properly intended to be within the full range of equivalents of the following claims.

What is claimed is:

1. In a process for oligomerizing olefins by contacting an olefin with a solid phosphoric acid catalyst in an oligomerization reaction zone at a reaction temperature of 150° C. to 230° C. to form an olefin oligomerization product containing phosphorous-containing foulant precursors, said precursors being phosphoric acid esters the improvement which comprises removing at least a portion of said phosphorous-containing foulant precursors by contacting said olefin oligomerization product with a foulant adsorbent consisting of at least one member selected from the group consisting of alumina, activated alumina and magnesium oxide in an amount and under conditions sufficient to effect removal of at least a portion of said foulant precursors.

2. The process according to claim 1 wherein said phosphoric acid catalyst is a solid catalyst and wherein said olefin reaction is effected within a reactor comprising an olefin oligomerization zone and a foulant removal zone, said foulant removal zone containing said foulant adsorbent for removal of at least a portion of said phosphorous-containing foulant precursors from said olefin oligomerization product following removal of said olefin oligomerization product from said olefin reaction zone.

3. The process according to claim 1 wherein said phosphoric acid catalyst comprises a solid catalyst and wherein said olefin oligomerization product is removed from said olefin reaction zone and passed to a separate vessel for contact with said foulant adsorbent.

4. The process according to claim 2 or 3 wherein said foulant adsorbent is employed in an amount of from about 0.01 to 1.0 part by weight of said foulant adsorbent per part by weight of said phosphoric acid catalyst.

5. The process according to claim 2 or 3 wherein said contacting of said olefin oligomerization product with said foulant adsorbent effects the removal of at least about 20 wt. % of said phosphorous-containing foulant precursors.

6. In a process for oligomerizing olefins by contacting an olefin feed with a solid phosphoric acid catalyst in an oligomerization reaction zone at a reaction temperature of 150° C. to 230° C. to form an olefin oligomerization product containing phosphorous-containing foulant precursors, said precursors being phosphoric acid esters the improvement which comprises contacting said olefin oligomerization product with a foulant adsorbent consisting of at least one member selected from the group consisting of alumina, activated alumina and magnesium oxide to effect removal of at least about 50 wt. % of said phosphorous-containing foulant precursors, said foulant adsorbent being employed in an amount of from about 0.05 to 0.2 part by weight of said phosphoric acid catalyst.

7. The process according to claim 6 wherein a treated olefin oligomerization product is formed after contact with said foulant adsorbent for a time and under conditions sufficient to reduce the concentration of said phosphorous-containing foulant precursors to a level of less than about 100 ppm by weight.

* * * * *